US008198354B2

(12) United States Patent
Miller et al.

(10) Patent No.: US 8,198,354 B2
(45) Date of Patent: Jun. 12, 2012

(54) PHARMACEUTICAL METERED DOSE INHALER AND METHODS RELATING THERETO

(75) Inventors: John Francis Miller, Durham, NC (US); Mark Lee Sommerville, Durham, NC (US)

(73) Assignee: Glaxo Group Limited, Greenford, Middlesex (GB)

( * ) Notice: Subject to any disclaimer, the term of this patent is extended or adjusted under 35 U.S.C. 154(b) by 982 days.

(21) Appl. No.: 10/568,051

(22) PCT Filed: Aug. 11, 2004

(86) PCT No.: PCT/US2004/026252
§ 371 (c)(1),
(2), (4) Date: Feb. 10, 2006

(87) PCT Pub. No.: WO2005/016410
PCT Pub. Date: Feb. 24, 2005

(65) Prior Publication Data
US 2007/0112114 A1 May 17, 2007

Related U.S. Application Data

(60) Provisional application No. 60/494,450, filed on Aug. 11, 2003.

(51) Int. Cl.
C08K 5/05 (2006.01)
(52) U.S. Cl. ........ 524/379; 524/300; 524/323; 528/495; 528/496
(58) Field of Classification Search .............. 524/300, 524/323, 379; 528/495, 496
See application file for complete search history.

(56) References Cited

U.S. PATENT DOCUMENTS

| 4,352,789 | A | 10/1982 | Thiel |
| 5,126,123 | A | 6/1992 | Johnson |
| 5,182,097 | A | 1/1993 | Byron et al. |
| 5,376,359 | A | 12/1994 | Johnson |
| 5,427,282 | A * | 6/1995 | Greenleaf et al. ......... 222/402.1 |
| 5,550,211 | A | 8/1996 | DeCrosta et al. |
| 5,861,473 | A | 1/1999 | DeCrosta et al. |
| 6,068,789 | A | 5/2000 | Barnes et al. |
| 6,119,853 | A | 9/2000 | Garrill et al. |
| 6,241,828 | B1 | 6/2001 | Barnes et al. |
| 6,451,287 | B1 | 9/2002 | Desimone et al. |
| 2004/0050960 | A1 | 3/2004 | Godfrey et al. |
| 2005/0092679 | A1 | 5/2005 | Warby |

FOREIGN PATENT DOCUMENTS

| EP | 0134847 A1 | 3/1985 |
| EP | 0134847 B1 | 3/1985 |
| EP | 0372777 A2 | 6/1990 |
| JP | 2001512499 | 8/2001 |
| WO | 9104011 A1 | 4/1991 |
| WO | 9111173 A1 | 8/1991 |
| WO | 9111495 A1 | 8/1991 |
| WO | 9114422 A1 | 10/1991 |
| WO | 9200061 A1 | 1/1992 |
| WO | 9200062 A1 | 1/1992 |
| WO | 9312161 A1 | 6/1993 |
| WO | 9609816 A1 | 4/1996 |
| WO | 9632099 A1 | 10/1996 |
| WO | 9632150 A1 | 10/1996 |
| WO | 9632151 A1 | 10/1996 |
| WO | 9632345 A1 | 10/1996 |
| WO | 97/48754 A1 | 12/1997 |
| WO | 98/33827 | 8/1998 |
| WO | 02051483 A1 | 7/2002 |
| WO | 02/72448 A1 | 9/2002 |
| WO | 02072448 A1 | 9/2002 |
| WO | 03/49786 A2 | 6/2003 |
| WO | 03049786 A2 | 6/2003 |

OTHER PUBLICATIONS

ITFG/IPAC-RS Collaboration—CMC Leachables and Extractables Technical Team; "Leachables and Extractables Testing: Points to Consider"; A Response to the FDA draft Guidances for Industry; Mar. 27, 2001; pp. 1-36; <www.fda.gov/ohrms/dockets/ac/00/reports/3657_rpt1.pdf>.

Joseph H. Groeger & Leslie M. Compton; "Identifying and Preventing Contamination from Pharmaceutical Packaging"; Medical Plastics and Biomaterials Magazine; May 1997; <www.devicelink.com/mpb/archive/97/05/005.html>.

U.S. Department of Health and Human Services—Food and Drug Administration—CDER; "Draft Guidance for Industry—Metered Dose Inhaler (MDI) and Dry Powder Inhaler (DPI) Drug Products"; Chemistry, Manufacturing, and Controls Documentation; Oct. 1998; pp. 1-62; <www.fda.gov/Cder/guidance/2180dft.pdf>.

Figazette, A., M. McLoughlin, R. Renfrow, and T. Rossi; "Analysis of Extractables from Nitrile Rubber Components in Metered Dose Inhalers"; Pharmaceutical Analysis Department, SmithKline Beecham Pharmaceuticals, King of Prussia, PA, presented at the Symposium—Regulatory Issues in Aerosol Drug Development on Jun. 12-14, 1991 in Arlington, VA by the University of Kentucky College of Pharmacy.

U.S. Appl. No. 10/566,457, filed Jan. 30, 2006.

(Continued)

Primary Examiner — Edward Cain
(74) Attorney, Agent, or Firm — Robert J. Smith

(57) ABSTRACT

Methods of preparing elastomeric gasket materials for use in metered dose inhalers that include contacting an elastomeric gasket material to be used in a metered dose inhaler, which gasket material comprises one or more extractable compounds, with a solution comprising an organic solvent under conditions sufficient to extract at least a portion of at least one of the one or more extractable compounds from the elastomeric gasket material are described. Sealing gaskets made by such methods as well as metering valves, metered dose inhalers, and drug products that include such gaskets are also described.

28 Claims, 5 Drawing Sheets

OTHER PUBLICATIONS

Figure 1:
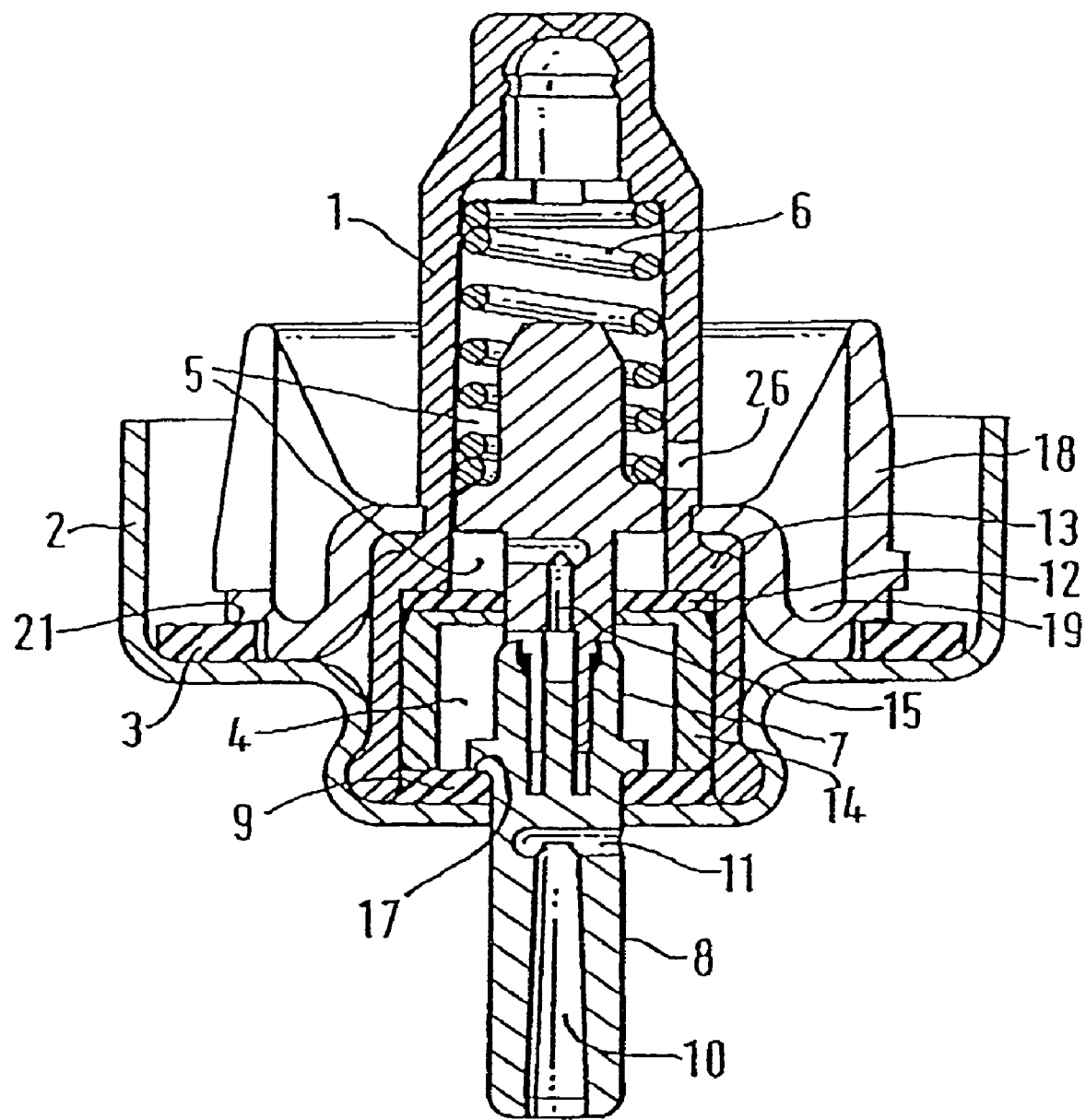

Graziano; Ethanol Extraction of Rubber Components; Bespak Drug Delivery Technologies Regulatory Compliance; QA3300 Issue 1; Mar. 13, 2003.

"Pharmaceutical metering valves: for a wide spectrum of HFC/HFA usage" Bespak Drug Delivery Technologies, Aug. 2000.

FSW Group Limited; Invoice # 304007; Aug. 25, 2000; to Bespak Europe Limited; Reprinting Costs for Bespak Literature.

Figazette, A., M. McLoughlin, R. Renfrow, and T. Rossi, "Analysis of Extractables from Nitrile Rubber Components in Metered Dose Inhalers" Pharmaceutical Analysis Department, SmithKline Beecham Pharmaceuticals, King of Prussia, PA, presented at the Symposium—Regulatory Issues in Aerosol Drug Development on Jun. 12-14, 1991 in Arlington, VA by the University of Kentucky College of Pharmacy.

* cited by examiner (Experiment H)

(Experiment I)

(Experiment J)

PHARMACEUTICAL METERED DOSE INHALER AND METHODS RELATING THERETO

This application is filed pursuant to 35 U.S.C. §371 as a United States National Phase Application of International Patent Application Serial No. PCT/US2004/026252 filed Aug. 11, 2004, which claims priority from Provisional Application No. 60/494,450 filed Aug. 11, 2003.

The present invention relates to methods of treating metered dose inhaler (MDI) sealing gaskets and MDI sealing gaskets made from treated materials. The invention further relates to a container for an MDI with enhanced characteristics and methods associated therewith. The MDI is typically one for use in dispensing a quantity of a medicament-containing formulation which may be used in the treatment of respiratory or other disorders.

BACKGROUND

The use of aerosols to administer medicaments has been known for several decades. Such aerosols generally comprise the medicament, one or more chlorofluorocarbon propellants and one or more additives, for example a surfactant or a co-solvent, such as ethanol. Historically the most commonly used aerosol propellants for medicaments have been propellant 11 ($CCl_3F$), propellant 114 ($CF_2ClCF_2Cl$), propellant 12 ($CCl_2F_2$) or combinations of those. However release of those propellants into the atmosphere is now believed to contribute to the degradation of stratospheric ozone and there is thus a need to provide aerosol formulations for medicaments which employ so called "ozone-friendly" propellants.

Containers for aerosol formulations commonly comprise a vial body (can or canister) coupled to a valve. The valve comprises a valve stem through which the formulations are dispensed. Generally the valve includes one or more rubber valve seals intended to allow reciprocal movement of the valve stem which prevents leakage of propellant from the container. Metered dose inhalers comprise a valve which is designed to deliver a metered amount of an aerosol formulation to the recipient per actuation. Such a metering valve generally comprises a metering chamber which is of a predetermined volume and which causes the dose per actuation to be an accurate, pre-determined amount.

The metering valve in a container is typically coupled to the canister with contact through a sealing gasket to prevent leakage of propellant and/or drug substance out of the container at the join. The gasket typically comprises an elastomeric material, for example low density polyethylene, chlorobutyl, acrylonitrile butadiene rubbers, butyl rubber, a polymer of ethylene propylene diene monomer (EPDM), neoprene or chloroprene. Such elastomeric materials may be carbon-black or mineral filled.

Valves for use in MDIs are available from various manufactures known in the aerosol industry; for example from Valois, France (e.g. DF10, DF30, DF60), Bespak plc, UK (e.g. BK300, BK356, BK357) or 3M-Neotechnic Limited, UK (e.g. Spraymiser™). The metering valves are used in association with commercially available canisters, for example metal canisters, for example aluminium canisters, suitable for delivering pharmaceutical aerosol formulations.

MDIs incorporating a valve seal or a sealing gasket as described above generally perform adequately with CFC propellants, such as propellant 11 ($CCl_3F$), propellant 114 ($CF_2ClCF_2Cl$), propellant 12 ($CCl_2F_2$). However, as mentioned above, there is a requirement to substitute so-called ozone-friendly propellants for CFC propellants in aerosols. A class of propellants which are believed to have minimal ozone-depleting effects in comparison to conventional chlorofluorocarbons comprise fluorocarbons and hydrogen-containing chlorofluorocarbons. That class includes, but is not limited to hydrofluoroalkanes (HFAs), for example 1,1,1,2-tetrafluoroethane (HFA134a), 1,1,1,2,3,3,3-heptafluoro-n-propane (HFA 227) and mixtures thereof. However, various problems have arisen with pharmaceutical aerosol formulations prepared using HFA propellants, in particular with regard to the stability of the formulations.

Pharmaceutical aerosol formulations generally comprise a solution or a suspension. A mixture of a suspension and a small amount of dissolved medicament is also possible, but generally undesirable (as described below). Some solution formulations have the disadvantage that the drug substance contained therein is more susceptible to degradation than when in solid form. Furthermore, solution formulations may be associated with problems in controlling the size of the droplets which in turn affects the therapeutic profile. Suspension formulations are thus generally preferred.

To obtain regulatory approval, pharmaceutical aerosol formulation products must satisfy strict specifications. One parameter that must generally be satisfied, and for which a level is usually specified, is the fine particle mass (FPM). The FPM is a measure of the amount of drug that has the potential to reach the inner lungs (the small bronchioles and alveoli) based on the proportion of drug particles with a diameter within a certain range, usually less than 5 microns. The FPM of an actuation from an MDI is generally calculated on the basis of the sum of the amount of drug substance deposited on stages 3, 4 and 5 of an Andersen Cascade Impaction stack as determined by standard HPLC analysis. Potential side effects are minimised and a smaller amount of drug substance is wasted if the FPM constitutes as large as possible a percentage of the total mass of drug.

In suspension formulations, particle size of the emitted dose is generally controlled during manufacture by the size to which the solid medicament is reduced, usually by micronisation. During storage of some drug suspensions in an HFA, however, various changes have been found to take place which have the effect of reducing FPM. A drop in FPM means that the therapeutically effective amount of drug available to the patient is reduced. That is undesirable and may ultimately impact on the effectiveness of the medication. That problem is particularly acute when the dose due to be dispensed is low, which is the case for certain potent drugs such as long acting beta agonists, which are bronchodilators.

Various mechanisms have been proposed by which the reduction in FPM may be taking place: particle size growth may occur if the suspended drug has a sufficient solubility in propellant, a process known as Ostwald Ripening. Alternatively, or additionally, small particles may have the tendency to aggregate or adhere to parts of the inside of the MDI, for example the canister or valve. Small particles may also become absorbed into or adsorbed onto rubber components of the valve. As adherence and absorption processes are more prevalent amongst small particles, those processes lead to a decrease in FPM as a fraction of the administered drug as well as a reduction in the total drug content (TDC) of the canister available to patient. It has further been found that the adherence and absorption processes may not only result in loss of available drug, but may also adversely affect the function of the device, resulting in the valve sticking or orifices becoming blocked.

It is essential that the prescribed dose of aerosol medication delivered from the MDI to the patient consistently meets the specifications claimed by the manufacturer and complies with the requirements of the FDA and other regulatory authorities. That is, every dose dispensed from the MDI must be the same within close tolerances. Therefore it is important that the formulation be substantially homogenous throughout the canister and the administered dose at the time of actuation of the metering valve and that it remains substantially the same even after storage.

Various approaches have been taken to address the problems mentioned above. One approach is the addition of one or more adjuvants to the drug suspension; for example adjuvants selected from alcohols, alkanes, dimethyl ether, surfactants (e.g. fluorinated or non-fluorinated surfactants, carboxylic acids, polyethoxylates, etc.) and even conventional chlorofluorocarbon propellants in small amounts (at levels intended to keep to a minimum potential ozone damage) have been shown to have some effect in mitigating the FPM problems. Such approaches have been disclosed, for example, in EP0372777, WO91/04011, WO91/11173, WO91/11495 and WO91/14422. WO92/00061 discloses non-fluorinated surfactants for use with fluorocarbon propellants. Fluorinated surfactants may be used to stabilise micronised drug suspensions in fluorocarbon propellants such as 1,1,1,2-tetrafluoroethane (P134a) or 1,1,1,2,3,3,3-heptafluoro-n-propane (P227), see for example U.S. Pat. Nos. 4,352,789, 5,126,123, 5,376,359, U.S. application Ser. No. 09/580,008, WO91/11173, WO91/14422, WO92/00062 and WO96/09816.

In WO96/32345, WO96/32151, WO96/32150 and WO96/32099 there are disclosed aerosol canisters coated with one or more fluorocarbon polymers, optionally in combination with one or more non-fluorocarbon polymers, that reduce the deposition on the canister walls of drug particles of the pharmaceutical alternative propellant aerosol formulation contained therein.

In WO 03/049786 it is described that deposition of drug on an elastomeric seal, and several other problems associated with lubrication, flexibility and sealing ability of an elastomeric seal may be overcome by the addition of an organotitanium low friction barrier coating to the seal surface. A pre-treatment step in which the elastomeric seal is treated as follows is also disclosed therein: the elastomeric substrate Is provided in a bath comprising an alcohol and an alkaline material at a bath temperature effective for treatment, ultrasonic energy is provided to the bath at a treatment effective frequency and power level for a time sufficient to treat the elastomeric substrate, the treated elastomeric substrate is rinsed with de-ionised water; and the treated and rinsed elastomeric substrate is dried. The pre-treatment step is said to permit superior adhesion and bonding of the organotitanium-based coating. In general, however, additional material coating steps add to the expense of manufacturing the final drug product and the presence of a coating may cause additional toxicity and safety tests to be necessary.

The present invention is concerned with an alternative, less burdensome procedure for treating MDI seals, and methods and articles associated therewith.

SUMMARY OF THE INVENTION

According to embodiments of the present invention, a method of preparing an elastomeric gasket material for use in a metered dose inhaler includes contacting an elastomeric gasket material to be used in a metered dose inhaler, which gasket material comprises one or more extractable compounds, with a solution comprising an organic solvent under conditions sufficient to extract at least a portion of at least one of the one or more extractable compounds from the elastomeric gasket material. In some embodiments, at least 10, 15, 20, 25, 30, 35, 40, 45, 50 or more percent of the one or more extractable compounds is extracted from the elastomeric gasket material.

It has surprisingly been found that an MDI sealing gasket that has been treated in accordance with embodiments of the present invention has advantageous properties in use. The drop in FPM after prolonged storage of drug substance was reduced in an MDI comprising one or more sealing gaskets according to embodiments of the present invention in comparison with the effects observed after storage in an MDI with untreated gaskets. It has also been found that the absolute FPM measurements (before or after storage) were higher in an MDI comprising one or more treated gaskets according to embodiments of the present invention than in an MDI with untreated gaskets. Without being bound by any particular theory, it is, at the time of filing, hypothesised that embodiments of the present invention provide advantageous stabilisation of the aerosol formulation by one or more of the following effects: reducing drug deposition, improving stability of FPM even after storage, decreasing the increase in mean mass aerodynamic diameter (MMAD) during storage, and/or decreasing the GSD (Geometric Standard Deviation). It is further hypothesised that the one or more effects are caused by removal from the gasket of fatty acids and/or other leachable materials.

Preferably, the MDI sealing gasket is prepared according to embodiments of methods of the present invention before being utilized in a metering valve. Alternatively, the MDI sealing gasket can be prepared according to embodiments of methods of the present invention whilst being a part of a metering valve.

According to other embodiments of the present invention, a method of making an elastomeric sealing gasket for use in a metered dose inhaler includes contacting an elastomeric gasket material configured to be used in a metered dose inhaler, which gasket material comprises one or more extractable compounds, with a solution comprising an organic solvent under conditions sufficient to extract a portion of at least one of the one or more extractable compounds from the elastomeric gasket material, and forming a sealing gasket from the elastomeric gasket material. In some embodiments, the contacting of the elastomeric gasket material occurs after the forming of the sealing gasket. The process of forming the sealing gasket can include various processes as will be understood by those skilled in the art including cutting or punching the sealing gasket material to provide the sealing gasket.

Preferably, the elastomer is provided as a sheet. The sheet preferably has a thickness between 0.5 and 2 mm. Optionally, the elastomer may be provided in the form of a tube.

According to still other embodiments of the present invention, a method of making an elastomeric MDI sealing gasket includes forming an MDI gasket from a piece of elastomer that comprises one or more extractable compounds and has been contacted with a solution comprising an organic solvent under conditions sufficient to extract a portion of at least one of the one or more extractable compounds from the elastomeric gasket material.

According to yet other embodiments of the present invention, a method of making an elastomeric MDI sealing gasket includes contacting a base polymer starting material that comprises one or more extractable compounds with a solution comprising an organic solvent under conditions sufficient to extract at least a portion of at least one of the one or more extractable compounds from the base polymer starting material to provide a treated raw polymer material, producing elastomer from the treated raw polymer material; and forming an MDI gasket from the elastomer.

According to still other embodiments of the present invention, a method of making an elastomeric MDI sealing gasket includes forming an MDI gasket from a piece of elastomer that has been produced from base polymer starting material that comprises one or more extractable compounds and has been contacted with a solution comprising an organic solvent under conditions sufficient to extract at least a portion of at least one of the one or more extractable compounds from the base polymer starting material.

The solution can comprise various organic solvents that are capable of extracting one or more extractable compounds from the elastomeric gasket material and/or the base polymer starting material. Such solvents include, but are not limited to, lower alcohols such as methanol, ethanol, propanol (e.g., isopropanol), butanol (all isomers) or pentanol (all isomers), or solvents such as tetrahydrofuran, methylene chloride, acetone and other lower ketones (e.g., methyl ethyl ketone, isopropylmethylketone, etc.), ethers (e.g., ethyl ether, and other aliphatic and aromatic ethers), aromatic solvents (such as benzene, toluene, etc) and other common solvents. The organic solvent is preferably a lower alcohol, is more preferably ethanol or isopropanol, and is still more preferably ethanol. The lower alcohol (e.g., ethanol) is preferably an anhydrous lower alcohol. In some embodiments, the solution consists essentially of the organic solvent. In other embodiments, the solution consists of the organic solvent. In a preferred embodiment, the solution consists of anhydrous ethanol.

In some embodiments, the solution comprises an additive that may improve the solutions ability to extract one or more extractable compounds from the elastomeric gasket material and/or the base polymer starting material. For example, the solution can further comprise an acid or a base. The acid may be selected from various acids including, but not limited to, hydrochloric acid, acetic acid, sulfuric acid, nitric acid, and phosphoric acid. The acid is preferably used at a concentration such that the solution has a pH of from a lower limit of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 to an upper limit of 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9. The base may be selected from various bases including, but not limited to, alkali metal hydroxides such as sodium hydroxide. The base is preferably used at a concentration such that the solution has a pH of from a lower limit of 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, or 11.9 to an upper limit of 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, or 13.0.

Preferably, the contacting of the elastomeric gasket material or the base polymer starting material with the solution in methods according to embodiments of the present invention is carried out at a temperature of from 20° C. to the boiling point of the solution. More preferably, the contacting process is carried out at a temperature of from 40° C. to the boiling point. Still more preferably, the contacting process is carried out at a temperature of from 60° C. to boiling point. Even more preferably, the contacting process takes place under reflux. The present inventors have found that the amount of various extractable compounds removed from the elastomeric gasket material over a given period of time is temperature dependent, with higher temperatures generally resulting in a larger amount of extractable compounds removed.

In some embodiments, the contacting process is carried out for 15 minutes or more (e.g., from 15 minutes to 48 hours). Preferably, the contacting process is carried out for from 1 to 12 hours, more preferably from 2 to 10 hours, still more preferably from 4 to 8 hours, for example approximately 6 hours.

For a particular elastomeric gasket material treated by processes according to embodiments of the present invention to be useful as a sealing gasket in an MDI, the contacting process parameters of time, temperature, and solvent should be selected to balance the desire of stabilising the aerosol formulation by removing one or more extractable compounds from the elastomeric gasket material with the need for the elastomeric gasket material to retain its physical properties so that it can function as a sealing gasket for the MDI. For example, when the elastomeric gasket material is EPDM and the solution is ethanol, the contacting process can be carried out at from 60° C. to the boiling point of ethanol for a period of 12 to 30 hours to provide a sealing gasket that will aid in stabilising the aerosol formulation while retaining its physical properties as a sealing gasket for an MDI. An elastomeric gasket material's ability to retain its physical properties as a sealing gasket for an MDI can be determined by various methods as will be understood by those skilled in the art, such as placing the treated gasket into an MDI, filling the MDI with HFA propellant (alone or in combination with a medicament), and measuring the leak rate of the propellant and/or the moisture ingress into the MDI. Leak rate and moisture ingress can be determined by methods known to those skilled in the art. One skilled in the art will be able to use the disclosure provided herein to readily determine the appropriate process parameters for a given elastomeric gasket material and a given aerosol pharmaceutical formulation.

The contacting process according to embodiments of the present invention can be performed as a batch process or a continuous process as will be understood by those skilled in the art. When the contacting process is performed as a batch process, the methods according to the present invention may include more than one contacting process (e.g., 2, 3, 4, 5, 6 or more contacting processes) wherein the same elastomeric material is contacted more than once. A continuous contacting process is preferred. Equipment for use in batch or continuous contacting processes is known to those skilled in the art.

In embodiments according to the present invention, methods of preparing a sealing gasket that includes an elastomeric gasket material comprises contacting the sealing gasket, which comprises one or more extractable compounds, with a solution comprising an organic solvent under conditions sufficient to extract at least a portion of at least one of the one or more extractable compounds from the sealing gasket, and agitating the sealing gasket. The agitation process can be performed concurrently with the contacting process or sequentially with the contacting process. In some embodiments, elastomeric gasket material in the form of sealing gaskets is placed into a column and the solution comprising an organic solvent is flowed through the column. After a period of time, such as 2, 3, 4, 5, or 6 hours, the elastomeric sealing gaskets are removed from the column and agitated for a period of time, such as 5, 10, 15, or 20 to 30, 40, 50, or 60 minutes. The agitation can be provided by various means as will be understood by those in the art such as, but not limited to, placing the sealing gaskets in an explosion proof dryer.

The contacting process and agitation process may be repeated 2, 3, 4, 5, 6, 7, 8 or more times.

The methods according to the present invention can include the process of distilling the solution after it has contacted the elastomeric gasket material or the base polymer starting material and utilizing the distilled solution to re-contact the material (e.g., in the same or a subsequent batch contacting process or as part of the continuous contacting process). When the material includes an extractable material having a vapor pressure that is higher than the vapor pressure of the solution (or, in some embodiments, of the organic solvent in the solution), it is preferable not to distill and re-use the solution, but instead to use fresh solution (i.e., solution that has not been previously used to contact an elastomeric gasket material or a base polymer starting material) for the contacting process(es).

The contacting process according to embodiments of the present invention can be performed in an oxygen-containing atmosphere (e.g., air) or in an inert atmosphere. The inert atmosphere can be provided by various means such as an inert gas or by performing the contacting process as part of a sealed, continuous process.

The elastomeric gasket material may be one comprising low density polyethylene, chlorobutyl or acrylonitrile butadiene rubber, butyl rubber, a polymer of ethylene propylene diene monomer (EPDM), neoprene or chloroprene. The elastomeric material may be carbon-black or mineral filled. Preferably the elastomeric gasket material is one made from an acrylonitrile butadiene polymer (also known as an acrylonitrile butadiene rubber) or a polymer of ethylene propylene diene monomer (EPDM). More preferably the material is an acrylonitrile butadiene polymer.

Extractable compounds according to embodiments of the present invention include various compounds typically found in elastomeric gasket materials that are capable of being extracted from the materials using an organic solvent. Such compounds include, but are not limited to, fatty acids, antioxidants, light stabilizing compounds, rubber synthesis byproducts, and other rubber extractables. The extractable compounds are preferably nonylphenol isomers, 2,2'-methylenebis(6-tertbutyl-4-methylphenol), 2,2,4,6,6-pentamethylhept-3-ene, 3'-oxybispropanitrile, oleic acid, palmitic acid, elaidic acid, and stearic acid, and are more preferably 2,2'-methylenebis(6-tertbutyl-4-methylphenol), 2,2,4,6,6-pentamethylhept-3-ene, 3'-oxybispropanitrile, and oleic acid. In some embodiments, the extractable compounds include tris (2,4-di-tert-butylphenyl)phosphate, tris (2,4-di-tert-butylphenyl)phosphate, 3,5-di-tert-butylphenol, 2,4-di-tert-butylphenol, and/or 4-methyl-2,6-di-tert-butylphenol in addition to one or more of the foregoing extractable compounds. In other embodiments, the extractable compounds include eicosanol, docosanol, dodecanol, or other fatty alcohols in addition to one or more of the foregoing extractable compounds. In some embodiments according to the present invention, the extractable compounds include one or more compounds having a vapor pressure that is greater than 45 torr (6,000 Pa), such as 2,2,4,6,6-pentamethylhept-3-ene, and 3'-oxybispropanitrile.

In some embodiments, the contacting process is the last treatment process that significantly affects the properties of the elastomeric gasket material. Further optional steps may include rinsing the treated elastomeric gasket material with a neutralising solution (which is preferred when the solution includes a pH modifier), rinsing the treated elastomeric gasket material with water (for example distilled or de-ionised water), or rinsing the treated elastomeric gasket material with a rinsing solution comprising an organic solvent such as those described above with respect to the contacting process, and drying the rinsed elastomeric gasket material (e.g., by exposing the material to heat in, for example, a drying oven). The organic solvent in the rinsing solution may be the same as or different from the organic solvent in the contacting solution. Preferably, the organic solvent in the rinsing solution and the contacting solution are the same. In an embodiment of the present invention, the contacting solution consists essentially of an organic solvent as described above and the preparation or treatment method does not include a rinsing process. In a preferred embodiment of the present invention, the contacting solution consists essentially of an organic solvent as described above and the preparation or treatment method includes a rinsing process that comprises rinsing the treated elastomeric gasket material with a rinsing solution comprising an organic solvent. In such methods, the drying process may be performed by exposing the elastomeric gasket material to a vacuum, such as a vacuum of less than 1, 2, 3, 4, or 5 mm Hg. This vacuum drying process may be more efficient (e.g., energy and/or time efficient) than the heat drying process that may be needed if a rinse process is utilized.

Other treatment steps may be included in the overall treatment process. The elastomeric gasket material may, for example, be washed with detergent and or bleach. Such a washing process preferably occurs prior to the contacting of the elastomeric gasket material with the solution comprising the organic solvent. It is preferred that the elastomeric gasket material is not coated with an organotitanium coating. It is preferred that the treatment in accordance with the invention does not include providing ultrasonic energy to the elastomer.

According to embodiments of the present invention, a sealing gasket for use in an inhaler is provided which seal has been prepared by a method in accordance with embodiments of the present invention or has been made by a method in accordance with embodiments of the present invention. As used herein, the term "gasket" is used interchangeably with the terms "sealing gasket" or "seal".

In some embodiments, the sealing gasket for use in a metered dose inhaler includes a treated elastomeric gasket material comprising one or more extractable compounds, wherein the level of at least one of the one or more extractable compounds present in the treated elastomeric gasket material is at least 5 percent less than the level of the at least one of the one or more extractable compounds that would be present if the elastomeric gasket material were untreated. As used herein, the term "treated elastomeric gasket material" includes elastomeric gasket material prepared or made according to embodiments of the present invention. In some embodiments, the level of at least one of the one or more extractable compounds is at least 10, 15, 20, 25, 30, 35, 40, 45, 50 or more percent less than the level of the at least one of the one or more extractable compounds that would be present if the elastomeric gasket material were untreated. The extractable compounds are as described above. In some embodiments, at least one of the one or more extractable compounds has a vapor pressure that is greater than 45 torr (6,000 Pa) as described above.

In some embodiments, a gasket for use in a metered dose Inhaler comprises an elastomeric gasket material and between about 0.001 and 1 percent (by weight of the gasket) of one or more extractable compounds. The extractable compounds are as described above. In some embodiments, the gasket comprises an amount between a lower limit of 0.001, 0.005, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85 or 0.9 and an upper limit of 0.005, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 2, 3, 4, 5, 6, 7, 8, 9, or 10 percent (by weight of the gasket) of one or more of the extractable compounds. In some embodiments, at least one of the one or more extractable compounds has a vapor pressure that is greater than 45 torr (6,000 Pa) such as those described above.

According to some embodiments of the present invention, a method of manufacturing an MDI comprises providing an MDI sealing gasket that has been treated in accordance with the invention, providing the other MDI components and a pharmaceutical aerosol formulation and assembling the MDI. One skilled in the art will understand that the sealing gaskets according to embodiments of the present invention can be substituted for untreated gaskets in conventional MDIs.

The pharmaceutical aerosol formulation may comprises any suitable medicament, for example an anti-asthmatic, for example a bronchodilator or an anti-inflammatory, particularly of steroid type, having a local therapeutic action in the lungs and/or a systemic action after absorption into the blood. The pharmaceutical aerosol formulation may comprise salbutamol particularly as the sulphate, 3-(4-{[6-({(2R)-2-hydroxy-2-[4-hydroxy-3-(hydroxymethyl)phenyl]ethyl}amino)hexyl]oxy}butyl) benzenesulfonamide, 3-(3{-[7-({(2R)-2-hydroxy-2-[4-hydroxy-3-hydroxymethyl)phenyl]ethyl}-amino)heptyl]oxy}propyl) benzenesulfonamide, 4-{(1 R)-2-[(6-{2-[(2,6-dichlorobenzyl)oxy]ethoxy}hexyl)amino]-1-hydroxyethyl}-2-(hydroxymethyl)phenol, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, N-(3,5-dichloropyridin-4-yl)-2-[1-(4-fluorobenzyl)-5-hyroxyindol-3-yl]-2-oxoacetamide, a compound of formula (II) as disclosed in WO01/42193, a compound of formula (I) as disclosed in WO03/042160, or a compound of formula (I) as disclosed in WO03/042164.

Preferably, the pharmaceutical aerosol formulation comprises salmeterol xinafoate, fluticasone propionate or a combination of those with each other and/or with one or more further medicaments.

According to other embodiments of the present invention, a container comprises a canister sealed with a metering valve and a sealing gasket, which canister contains a pharmaceutical aerosol formulation comprising a propellant and a medicament, wherein the sealing gasket is one in accordance with the present invention. A container according to embodiments of the present invention is preferably a sealed container capable of withstanding the pressure required to maintain the propellant as a liquid. In some embodiments, the canister contains a pharmaceutical aerosol formulation comprising a propellant, a medicament and between a lower limit of 0.7, 0.8, 0.9, 1.0, 1.1, 1.2, 1.3, 1.4, or 1.5 and an upper limit of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0 µg of palmitic acid after storage at 40° C. for 2, 4, 8, or more weeks. In other embodiments, the canister contains a pharmaceutical aerosol formulation comprising a propellant, a medicament and between a lower limit of 0.7, 0.8, 0.9, 1.0, 1.1, 1.2, 1.3, 1.4, or 1.5 and an upper limit of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0 µg of oleic acid after storage at 40° C. for 2, 4, 8, or more weeks. In still other embodiments, the canister contains a pharmaceutical aerosol formulation comprising a propellant, a medicament and between a lower limit of 0.0, 0.1, or 0.2 and an upper limit of 0.2, 0.3, or 0.4 µg of elaidic acid after storage at 40° C. for 2, 4, 8, or more weeks. In some embodiments, the canister contains a pharmaceutical aerosol formulation comprising a propellant, a medicament and between a lower limit of 0.0, 0.1, 0.2, 0.3, 0.4, 0.5, 0.6, 0.7, 0.8, 0.9, 1.0, 1.1, 1.2, 1.3, 1.4, or 1.5 and an upper limit of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 µg of stearic acid after storage at 40° C. for 2, 4, 8, or more weeks. According to some embodiments of the present invention, the canister contains a pharmaceutical aerosol formulation comprising a propellant, a medicament, and two or more of palmitic acid, oleic acid, elaidic acid, and stearic acid, which fatty acids are present in the formulation in the applicable amount described above.

Especially preferred is a container with a metering valve comprising a metering chamber defined by walls and an upper and a lower sealing gasket through which passes a valve stem. Optionally, the one or more of the sealing gaskets within the metering valve may be sealing gaskets in accordance with the present invention.

In some embodiments, a medicament container for use in a metered dose inhaler includes a canister having an open end and a closed end, a metering valve that includes a valve body, a valve stem, and one or more stem seals in contact with the valve stem, where the valve body and at least one of the one or more stem seals define a metering chamber, a cap configured to seal the open end of the canister such that the sealed canister is adapted to contain an aerosol pharmaceutical composition; and a canister seal positioned between the open end of the canister and the cap, where at least one of the canister seal and the one or more stem seals comprise a sealing gasket according to the present invention. In some embodiments, the medicament container contains a pharmaceutical aerosol formulation as described herein. In other embodiments, the medicament container is empty and has not yet been filled with a pharmaceutical aerosol formulation.

According to other embodiments of the present invention, a process for making a container configured to contain a pharmaceutical aerosol formulation and provide metered doses thereof includes coupling a metering valve that comprises one or more stem seals to a canister to provide the container, wherein at least one of the one or more stem seals comprises a sealing gasket according to the present invention. The coupling process preferably includes coupling the metering valve to the canister utilizing a cap (or ferule) and canister seal configured to seal the canister such that the canister is adapted to contain an aerosol pharmaceutical composition.

According to still other embodiments of the present invention, a metering valve suitable for metering a drug suspension comprising a medicament and a propellant is provided, which metering valve comprises a valve body, a metering chamber, a valve stem and one or more sealing gaskets in accordance with the present invention. A metering valve according to embodiments of the invention incorporates a gasket to prevent leakage of propellant through the valve. Such a metering valve is preferably designed to deliver a metered amount of the formulation per actuation.

In some embodiments, the metering valve includes a valve body, a valve stem, and one or more stem seals in contact with the valve stem, at least one of the one or more stem seals comprising a sealing gasket according to the present invention, wherein the valve body and at least one of the one or more stem seals define a metering chamber.

In other embodiments, a process for making a metering valve is provided that includes assembling a valve body, a valve stem, and one or more stem seals to form a metering valve, wherein the valve body and at least one of the one or more stem seals define a metering chamber, and wherein at least one of the one or more stem seals is a sealing gasket according to the present invention.

According to yet other embodiments of the present invention, a metered dose inhaler comprises a canister in communication with a metering valve suitable for metering a drug suspension comprising a medicament and a liquid propellant, wherein the metering valve includes and/or the canister is sealed with a sealing gasket in accordance with the present invention. Metered dose inhalers are designed to deliver a fixed unit dosage of medicament per actuation or "puff", for example, in the range of 2.5 to 5000 micrograms of medicament per puff, preferably in the range of from 5.0 to 2500 micrograms per puff.

According to some embodiments of the invention, a drug product comprises a canister containing a drug suspension comprising a propellant and a medicament in communication with a metering valve suitable for metering a drug suspension comprising a medicament and a liquid propellant, wherein the metering valve and/or the canister are sealed with one or more sealing gaskets according to the present invention.

In some embodiments, a drug product includes a canister having an open end and a closed end, a metering valve that includes a valve body, a valve stem, and one or more stem seals in contact with the valve stem, where the valve body and at least one of the one or more stem seals define a metering chamber, a cap configured to seal the open end of the canister such that the sealed canister is adapted to contain an aerosol pharmaceutical composition, a canister seal positioned between the open end of the canister and the cap, and a valve actuator configured to actuate the metering valve and dispense a metered dose of the pharmaceutical aerosol formulation, where at least one of the canister seal and the one or more stem seals comprise a sealing gasket according to the present invention.

In other embodiments, a process for making a drug product includes assembling an actuator and a canister containing a pharmaceutical aerosol formulation to provide the drug product, wherein the canister comprises a canister seal and a metering valve comprising one or more stem seals, wherein one or more of the canister seal and the one or more stem seals comprise a sealing gasket according to the present invention.

According to some embodiments of the present invention, a package comprises a metered dose inhaler in accordance with the present invention contained within a flexible wrapper, said wrapper being composed of a material that is substantially permeable to evacuation of propellant gas and substantially impermeable to intrusion of atmospheric moisture e.g. as described in U.S. Pat. No. 6,119,853. Preferably the package will also contain within it a desiccant material. The desiccant material may be inside the MDI and/or outside the MDI.

According to embodiments of the present invention, a method of treating a respiratory disease such as asthma, rhinitis or COPD in a patient comprises use by the patient of a metered dose inhaler in accordance with the present invention.

In some embodiments, a method of treating and/or preventing the onset of a respiratory disease includes administering an effective amount of a pharmaceutical aerosol formulation to a person in need of treatment or prophylaxis of the respiratory disease, wherein the effective amount of the pharmaceutical aerosol formulation is administered from a metered dose inhaler that comprises a canister containing the pharmaceutical aerosol formulation, wherein the canister comprises a canister seal and a metering valve comprising one or more stem seals, wherein one or more of the canister seal and the one or more stem seals comprises a sealing gasket according to the present invention.

In a further aspect, embodiments of the invention provide a method of prolonging the shelf-life of a metered dose inhaler drug product comprising assembling the metered dose inhaler from parts including one or more sealing gaskets in accordance with the present invention.

In some embodiments, a method of prolonging the shelf-life of a metered dose inhaler drug product comprises assembling an actuator and a canister containing a pharmaceutical aerosol formulation to provide the metered dose inhaler drug product, wherein the canister comprises a canister seal and a metering valve comprising one or more stem seals, wherein one or more of the canister seal and the one or more stem seals comprise a sealing gasket according to the present invention.

Some embodiments of the invention provide the use of a gasket in accordance with the invention in a method of manufacturing an MDI for providing a dispensed drug aerosol with higher FPM than an MDI with an untreated seal or gasket. Embodiments of the invention provide the use of a gasket in accordance with embodiments of the invention in a method of manufacturing an MDI for providing a dispensed aerosol with an improved FPM storage stability in comparison with an MDI with an untreated sealing gasket. Some embodiments of the invention provide the use of a gasket in accordance with embodiments of the invention for increasing the shelf-life of a HFA suspension formulation in comparison with a corresponding formulation stored in a MDI with an untreated gasket.

Embodiments of the invention provide a sealing gasket comprising an elastomer characterised in that said gasket is a washed gasket from which 0.5% by weight or less such as 0.001 to 0.1% by weight of the gasket has been extracted with solution comprising an organic solvent.

According to other embodiments of the present invention, a container comprises a sealing gasket according to the present invention wherein said container is sealed with a metering valve and contains a pharmaceutical aerosol formulation comprising a particulate medicament and a liquefied HFA propellant, said container characterised in that the FPM of the particulate medicament is maintained within 15%, more preferably within 10% and especially within 5% of its original level after 4, 8, or preferably 12 weeks storage at 40° C. and 75% relative humidity. In some embodiments of the present invention, the particulate medicament comprises salmeterol, or a salt (e.g., xinafoate) thereof) and fluticasone propionate. In embodiments of the present invention in which the container is packaged in a flexible wrapper as described above with respect to the packaging of a metered dose inhaler, the container is preferably characterised in that the FPM of the particulate medicament is maintained within 15%, more preferably within 10% and especially within 5% of its original level after 4, 8, or preferably 12 weeks storage at 40° C., or 8, 24, or 52 weeks at room temperature.

According to still other embodiments of the present invention, a metered dose inhaler comprises a canister having an open end and a closed end, a metering valve that includes a valve body, a valve stem; and one or more stem seals in contact with the valve stem, where the valve body and at least one of the one or more stem seals define a metering chamber, a cap configured to seal the open end of the canister such that the sealed canister is adapted to contain an aerosol pharmaceutical composition, a canister seal positioned between the open end of the canister and the cap, and a valve actuator configured to actuate the metering valve and dispense a metered dose of the pharmaceutical aerosol formulation. At least one of the canister seal and the one or more stem seals comprises a sealing gasket according to the present invention, and the metered dose inhaler exhibits a change in fine particle mass (FPM) of less than 1, 5, 10, 15, 20, 30, 40, or 50 percent of the initial FPM after storage at 40° C. and 75 percent humidity for at least 4, 8, or 12 weeks.

According to embodiments of the present invention, a sealing gasket for use in an MDI includes an elastomeric gasket material and between a lower limit of 0.04, 0.05, 0.06, 0.07, 0.08, 0.09, 0.10, 0.11, 0.12, 0.13, or 0.14 and an upper limit of 0.09, 0.10, 0.11, 0.12, 0.13, 0.14, 0.15, 0.16, or 0.17% oleic acid by weight of the gasket. According to other embodiments of the present invention, a sealing gasket for use in an MDI includes an elastomeric gasket material as described above and between a lower limit of 0.05, 0.06, 0.07, 0.08, 0.09, 0.10, 0.11, 0.12, 0.13, 0.14, or 0.15 and an upper limit of 0.11, 0.12, 0.13, 0.14, 0.15, 0.16, 0.17; 0.18, 0.19, 0.20, 0.21, 0.22, 0.23, 0.24, 0.25, 0.26, 0.27, 0.28, 0.29, 0.30, 0.31, 0.32, 0.33, 0.34 and 0.35% palmitic acid by weight of the gasket. According to still other embodiments of the present invention, a sealing gasket for use in an MDI includes an elastomeric gasket material as described above and between a lower limit of 0.03, 0.04, 0.05, 0.06, 0.07, 0.08, 0.09, 0.10, 0.11, 0.12, or 0.13 and an upper limit of 0.08, 0.09, 0.10, 0.11, or 0.12% elaidic acid by weight of the gasket. According to yet other embodiments of the present invention, a sealing gasket for use in an MDI includes an elastomeric gasket material as described above and between a lower limit of 0.06, 0.07, 0.08, 0.09, 0.10, 0.11, 0.12, 0.13, 0.14, 0.15, 0.16, 0.17, 0.18, 0.19, 0.20 and an upper limit of 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, or 0.35% stearic acid by weight of the gasket. According to still other embodiments of the present invention, a sealing gasket for use in an MDI includes an elastomeric gasket material as described above and a mixture of two or more of oleic acid, palmitic acid, elaidic acid, and stearic acid, which acids are present in the applicable foregoing ranges. In a preferred embodiment, the sealing gasket for use in an MDI includes EPDM and 2, 3, or 4 of oleic acid, palmitic acid, elaidic acid, and stearic acid, which acids are present in the applicable foregoing ranges. While not wishing to be bound by theory, it is believed at this time that sealing gaskets for use in an MDI that have been subjected to an extraction process that results in the removal of one or more of the fatty acids described above to such an extent that the fatty acids are present in amounts below the foregoing lower limits may also result in the removal of other compounds, such as antioxidants, that act to stabilize the sealing gasket material. As a result of the removal of these other compounds, the sealing gaskets may experience a decrease in physical properties that may make the sealing gaskets unsuitable for use in an MDI. It is also believed that sealing gaskets for use in an MDI that include more than the foregoing amounts of fatty acids may result in a decreased stability of the aerosol pharmaceutical formulation over time.

The invention further provides the use of pure ethanol in a gasket extraction process for providing a seal or a gasket which, when incorporated into an MDI provides an MDI which has a dispensed drug aerosol with higher FPM than an MDI with an untreated sealing gasket. There is also provided the use of pure ethanol in a seal or gasket extraction process for providing a seal or a gasket which, when incorporated into an MDI provides an MDI which has a dispensed drug aerosol with an improved FPM storage stability in comparison with an MDI with an untreated sealing gasket.

The present invention finds particular application in MDIs for use with therapeutic agents that are antiasthmatics, including bronchodilators and antiinflammatories, particularly of steroid type, having a local therapeutic action in the lungs and/or a systemic therapeutic action after absorption in the blood. 4-Hydroxy-$\alpha^1$-[[[6-(4-phenylbutoxy)hexyl]amino]methyl]-1,3-benzene dimethanol was described as one of a wide range of bronchodilators in GB-A-2140800. That compound is also known by the generic name of salmeterol, the xinafoate salt of which has become widely known as a highly effective treatment of inflammatory diseases, such as asthma and chronic obstructive pulmonary disease (COPD). Fluticasone propionate is one of a range of topical anti-inflammatory corticosteroids with minimal liability to undesired systemic side effects which is described in GB-A-2088877, and is systematically named S-fluoromethyl 6$\alpha$, 9$\alpha$-difluoro-11$\beta$-hydroxy-16$\alpha$-methyl-17$\alpha$-propionyloxy-3-oxoandrosta-1, 4-diene-17$\beta$-carbothioate.

Preferably, the medicament is a combination of salmeterol xinafoate and fluticasone propionate. Preferably, no further medicament substances are present.

However, further to the medicaments already disclosed in this specification, MDIs of the present invention are also suitable for dispensing any medicaments which may be administered in aerosol formulations and useful in inhalation therapy e.g.; anti-allergics, e.g. cromoglycate (e.g. as the sodium salt), ketotifen or nedocromil (e.g. as sodium salt); anti-inflammatory steroids, e.g. beclomethasone (e.g. as dipropionate), fluticasone (e.g. as propionate), flunisolide, budesonide, rofleponide, mometasone (e.g as furoate), ciclesonide, triamcinolone acetonide; anticholinergics, e.g. ipratropium (e.g. as bromide), tiotropium, atropine or oxitropium and salts thereof. It will be clear to a person skilled in the art that, where appropriate, the medicaments may be used in the form of salts, (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant. Medicament may be used in the form of racemate or in the form of a pure isomer e.g. R-salmeterol or S-salmeterol. Formulations combining one or more the disclosed medicaments are also within the remit of this disclosure.

The container, MDI and valve described herein are particularly useful for medicaments which present similar formulation difficulties to those described above e.g. because of their susceptibility to water ingress, drug deposition, and other drug losses. Generally, those difficulties are especially severe for potent medicaments which are administered at low doses (i.e., less than about 1 mg per dose).

The particle size of the particulate (e.g. micronised) medicament should be such as to permit inhalation of substantially all of the medicament into the lungs upon administration of the aerosol formulation and will thus be less than 100 microns, desirably less than 20 microns, and preferably in the range 1-10 microns, e.g. 1-5 microns.

The concentration of medicament in the formulation will generally be 0.01-10% such as 0.01-2%, particularly 0.01-1%, especially 0.03-0.25% w/w. When salmeterol xinafoate is the only medicament, its concentration in the formulation will generally be 0.03-0.15% w/w.

The formulations according to the present invention may optionally contain one or more further ingredients conventionally used in the art of pharmaceutical aerosol formulation. Such optional ingredients include, but are not limited to, taste masking agents, sugars, buffers, antioxidants, water and chemical stabilisers.

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$. If desired the propellant may additionally contain a volatile adjuvant such as a saturated hydrocarbon, for example, propane, n-butane, isobutane, pentane and isopentane or a dialkyl ether, for example, dimethyl ether. In general, up to 50% w/w of the propellant may comprise a volatile hydrocarbon, for example 1 to 30% w/w. However, formulations which are substantially free of volatile adjuvants are preferred. In certain cases, it may be desirable to include appropriate amounts of water, which can be advantageous in modifying the dielectric properties of the propellant.

Polar adjuvants which may, if desired, be incorporated into the formulations according to the present invention include, for example, $C_{2-6}$ aliphatic alcohols and polyols such as ethanol, isopropanol and propylene glycol and mixtures thereof. Preferably, ethanol will be employed. In general only small quantities (e.g. 0.05 to 3.0% w/w) of polar adjuvants are required and the use of quantities in excess of 5% w/w may disadvantageously tend to dissolve the medicament. Formulations preferably contain less than 1% w/w, for example, about 0.1% w/w of polar adjuvant. Polarity may be determined, for example, by the method described in European Patent Application Publication No. 0327777. In some embodiments, it is desirable that the formulations of the invention are substantially free of polar adjuvants. "Substantially free" will generally be understood to mean containing less than 0.01% especially less than 0.0001% based on weight of formulation.

Preferably a single propellant is employed, for example, 1,1,1,2-tetrafluoroethane (HFA 134a) or 1,1,1,2,3,3,3-heptafluoro-n-propane (HFA 227), especially 1,1,1,2-tetrafluoroethane. It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

Whilst a suitable surfactant may be employed preferably the formulations of the invention are substantially free of surfactant. "Substantially free" will generally be understood to mean containing less than 0.01% w/w especially less than 0.0001% based on weight of formulation.

The formulations for use in the invention may be prepared by dispersal of the medicament in the selected propellant in an appropriate container, for example, with the aid of sonication or a high-shear mixer. The process is desirably carried out under controlled humidity conditions.

The term "sealing gasket" when used in this specification will be understood to mean a neck/canister gasket and/or lower sealing gasket and/or upper sealing gasket. The latter two gaskets being those associated with the metering chamber. According to some embodiments, in canisters according to the present invention the neck/canister gasket is the only gasket prepared according to the present invention.

The term "metered dose inhaler" or "MDI" means a unit comprising a canister, a secured cap covering the canister and a formulation metering valve situated in the cap. A fully assembled MDI includes a suitable channelling device. Suitable channelling devices comprise, for example, a valve actuator and a cylindrical or cone-like passage through which medicament may be delivered from the filled canister via the metering valve to the nose or mouth of a patient e.g. a mouthpiece actuator.

MDI canisters generally comprise a container capable of withstanding the vapour pressure of the propellant used such as a plastic or plastics-coated glass bottle or preferably a metal canister, for example, of aluminium or an alloy thereof which may optionally be anodised, lacquer-coated and/or plastic-coated (e.g. incorporated herein by reference WO96/32150 wherein part or all of the internal surfaces of the can are coated with one or more fluorocarbon polymers optionally in combination with one or more non-fluorocarbon polymers).

The cap may be secured onto the canister via welding such as ultrasonic welding or laser welding, screw fitting or crimping. MDIs taught herein may be prepared by methods of the art (e.g., see Byron, above and WO/96132150). Preferably the canister is fitted with a cap assembly, wherein a formulation metering valve is situated in the cap, and said cap is crimped in place.

The metering chamber (especially when composed of a plastics material) may be surface treated so as to present a substantially fluorinated surface to the formulation. Alternatively the metering chamber (especially when composed of a plastics material) may be surface treated with a siloxane such as dimethyl siloxane. As a further alternative, the metering chamber presents a substantially fluorinated surface to the formulation by virtue of being composed of a suitable substantially fluorinated material. Suitable metering chambers and surface treatments for metering chambers are described in WO 02/51483 at page 7, line 15 to page 11, line 18.

According to some embodiments of the present invention, a container as described above includes a valve stem that presents a substantially fluorinated surface to the formulation. Suitable valve stems and surface treatments for valve stems are described in WO 02/51483 at page 11, line 21 to page 12, line 3.

Preferably, containers according to embodiments of the invention comprise a canister composed of aluminium. Suitable surface treatments for a canister are described in WO 02/51483 at page 12, lines 10 to 16.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquefied propellant is pressure filled through the charge vessel into a manufacturing vessel, together with liquefied propellant containing the surfactant. The drug suspension is mixed before recirculation to a filling machine and an aliquot of the drug suspension is then filled through the metering valve into the canister.

In an alternative process, an aliquot of the liquefied formulation is added to an open canister under conditions which are sufficiently cold such that the formulation does not vaporise, and then a metering valve crimped onto the canister.

Typically, in batches prepared for pharmaceutical use, each filled canister is check-weighed, coded with a batch number and packed into a tray for storage before release testing.

Each filled canister is conveniently fitted into a suitable channelling device, prior to use, to form a metered dose inhaler system for administration of the medicament into the lungs or nasal cavity of a patient.

The chemical and physical stability and the pharmaceutical acceptability of the aerosol formulations according to the invention may be determined by techniques well known to those skilled in the art. Thus the chemical stability of the components may be determined by HPLC assay, for example, after prolonged storage of the product. Physical stability data may be gained from other conventional analytical techniques such as by leak testing, by valve delivery assay (average shot weights per actuation), by dose reproducibility assay (active ingredient per actuation) and spray distribution analysis.

The suspension stability of the aerosol formulations according to the invention may be measured by conventional techniques, for example, by measuring flocculation size distribution using a back light scattering instrument or by measuring aerodynamic particle size distribution by cascade impaction, next generation impactor, multistage liquid impinger, or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above. As discussed above, the absolute "fine particle mass" (FPM) is an important parameter in relation to the present invention. The FPM may be assessed using the same apparatus as the fine particle fraction.

Administration of medicament in a container or MDI in accordance with the invention may be indicated for the treatment of mild, moderate, severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example, from 1 to 8 times per day, giving for example 1, 2, 3 or 4 puffs each time.

Suitable daily doses, may be, for example, in the range 50 to 200 micrograms of salmeterol or 50 to 2000 micrograms of fluticasone propionate, depending on the severity of the disease. Thus, for example, each valve actuation may deliver 25 micrograms of salmeterol or 25, 50, 125 or 250 micrograms of fluticasone propionate. Doses for Seretide™, which is a combination of salmeterol (e.g. as xinafoate salt) and fluticasone propionate, will usually be those given for the corresponding individual component drugs. Typically each filled canister for use in a metered dose inhaler contains 60, 100, 120, 160 or 240 metered doses or puffs of medicament.

An appropriate dosing regime for other medicaments will be known or readily available to persons skilled in the art.

Except as otherwise noted, all references including patent and published patent applications referred to herein are incorporated herein by reference in their entireties.

The invention will now be described further with reference the following Examples which serve to illustrate the invention but is not intended to be limiting.

FIG. 1 shows part of a cross-section view of the valve end of an MDI container with the valve pointing downward. The main sealing gasket is represented by 3 the can/neck seal; The figure also shows the lower metering chamber seal 9 and the upper metering chamber seal 12.

FIG. 2 shows part of a cross-section view of the valve end of an alternative MDI container with the valve pointing downward.

FIG. 3 illustrates the fine particle mass ("FPM") for fluticasone propionate using controlled MDI gaskets and treated gaskets according to the invention.

FIG. 4 illustrates the fine particle mass ("FPM") for fluticasone propionate using controlled MDI gaskets and treated gaskets according to the invention.

FIG. 5 illustrates fine particle mass ("FPM") for fluticasone propionate using controlled MDI gaskets.

FIG. 6 illustrates fine particle mass ("FPM") for fluticasone propionate using treated MDI gaskets according to the invention.

FIG. 7 illustrates fine particle mass ("FPM") for fluticasone propionate using treated MDI gaskets according to the invention.

FIG. 8 illustrates fine particle mass ("FPM") for fluticasone propionate using treated MDI gaskets according to the invention.

Referring to FIG. 1, the valve body 1 is formed at its lower part with a metering chamber 4, and its upper part with a sampling chamber 5 which also acts as a housing for a return spring 6. The metering chamber is constructed from a fluorinated polymer at least in part and/or a fluorinated coating. The words "upper" and "lower" are used for the container when it is in a use orientation with the neck of the container and valve at the lower end of the container which corresponds to the orientation of the valve as shown in FIG. 1. Inside the valve body 1 is disposed a valve stem 7, a part 8 of which extends outside the valve through lower stem seal 9 and ferrule 2. The stem part 8 is formed with an inner axial or longitudinal canal 10 opening at the outer end of the stem and in communication with a radial passage 11.

The upper portion of stem 7 has a diameter such that it can slide through an opening in an upper stem seal 12 and will engage the periphery of that opening sufficiently to provide a seal. Upper stem seal 12 is held in position against a step 13 formed in the valve body 1 between the said lower and upper parts by a sleeve 14 which defines the metering chamber 4 between lower stem seal 9 and upper stem seal 12. The valve stem 7 has a passage 15 which, when the stem is in the inoperative position shown, provides a communication between the metering chamber 4 and sampling chamber 5, which itself communicates with the interior of the container via orifice 26 formed in the side of the valve body 1.

Valve stem 7 is biased downwardly to the inoperative position by return spring 6 and is provided with a shoulder 17 which abuts against lower stem seal 9. In the inoperative position as shown in FIG. 1 shoulder 17 abuts against lower stem seal 9 and radial passage 11 opens below lower stem seal 9 so that the metering chamber 4 is isolated from canal 10 and suspension inside cannot escape.

A ring 18 having a "U" shaped cross section extending in a radial direction is disposed around the valve body below orifice 26 so as to form a trough 19 around the valve body. As seen in FIG. 1 the ring is formed as a separate component having an inner annular contacting rim of a diameter suitable to provide a friction fit over the upper part of valve body 1, the ring seating against step 13 below the orifice 26. However, the ring 18 may alternatively be formed as an integrally moulded part of valve body 1.

To use the device the container is first shaken to homogenise the suspension within the container. The user then depresses the valve stem 7 against the force of the spring 6. When the valve stem is depressed both ends of the passage 15 come to lie on the side of upper stem seal 12 remote from the metering chamber 4. Thus a dose is metered within the fluorinated metering chamber. Continued depression of the valve stem will move the radial passage 11 into the metering chamber 4 while the upper stem seal 12 seals against the valve stem body. Thus, the metered dose can exit through the radial passage 11 and the outlet canal 10.

Releasing the valve stem causes it to return to the illustrated position under the force of the spring 6. The passage 15 then once again provides communication between the metering chamber 4 and sampling chamber 6. Accordingly, at this stage liquid passes under pressure from the container through orifice 26, through the passage 15 and thence into the metering chamber 4 to fill it.

Figure 2:
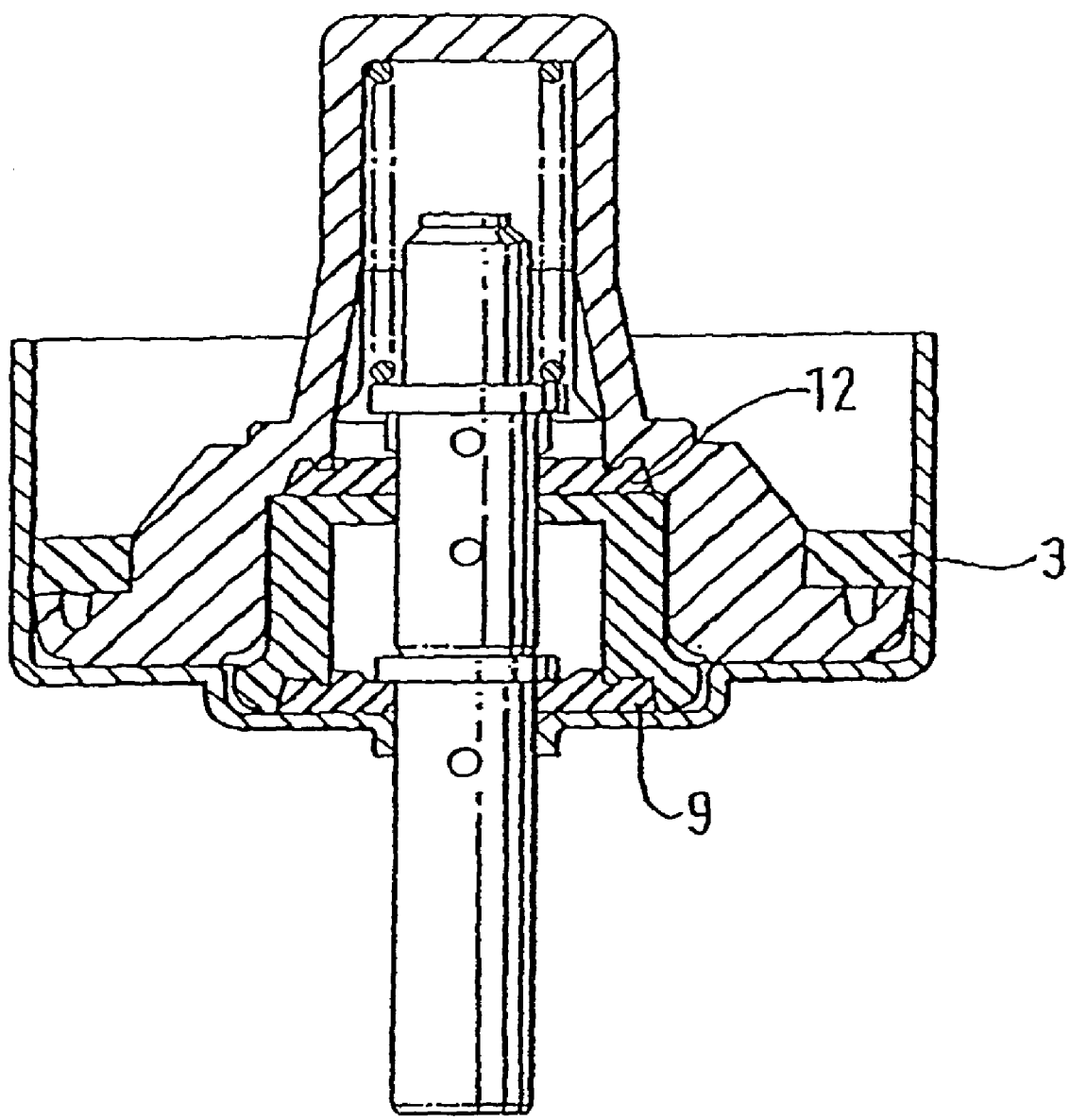

FIG. 2 shows a view of a different valve in which the gasket seal and lower and upper stem seals are labelled 3, 9 and 12 respectively.

EXAMPLES

Example 1

1. Treatment of Valve Gaskets

The valves used in the following experiments were DF60 valves from Valois (France). The cap sealing gasket (acrylonitrile butadiene polymer) was removed from the valve for treatment.

Experiment A

A 250 ml round bottomed flask was charged with 120 ml ethanol (anhydrous USP grade). 40 gaskets were placed in the solution and a condenser was attached to the flask. The solution was then heated under reflux for 1.5 hours with the exclusion of air. The hot ethanol was decanted and the gaskets were re-extracted using the same procedure. The gasket was then washed one time with 50 ml ethanol (anhydrous USP grade), removed from the round bottomed flask and dried in a vacuo over $CaSO_4$.

The gasket was then re-attached to the valve.

Experiment B

The treatment described above in respect of Experiment A was repeated using an ethanol-hydrochloric acid solution with an HCl concentration of 0.01 M HCl.

Experiment C

The treatment described above in respect of Experiment A was repeated using an ethanol-acetic acid solution with an AcOH concentration of 5% (v/v).

Experiment D

The treatment described above in respect of Experiment B was repeated. Instead of rinsing the gaskets with ethanol, the gaskets were immersed in de-ionized water and sodium hydroxide was added until the solution and gaskets were neutralized. The gaskets were dried over phosphorus pentoxide in vacuum.

Experiment E

The treatment describe above in respect of Experiment C was repeated. Instead of rinsing the gaskets with ethanol, the gaskets were immersed in de-ionized water and sodium hydroxide was added until the solution and gaskets were neutralized. The gaskets were dried over phosphorus pentoxide in vacuum.

Experiment F

Neck gaskets were placed in a Duran bottle and immersed in ethanol sufficient for total coverage. The bottles were then placed in an Ultrasonic batch (Decon FS200B) and sonicated on the high setting for 59 minutes. The ethanol was decanted off then replaced with fresh ethanol and allowed to stand for 2 hours with occasional swirling. The ethanol was again decanted off and the components then rinsed twice with fresh ethanol and then the components dried. The treated gaskets were then inserted into the valves.

Comparative Experiment G

The valve was left untreated.

2. Sample Preparation

The MDIs for which data are presented in Tables 1 and 2 were prepared in aluminium canisters coated with a PTFE/PES polymer blend as described in WO96/32150 and sealed with a valve prepared as described in 1 above. The aluminium canisters contained a pharmaceutical aerosol formulation comprising 4.2 mg of salmeterol in the form of its xinafoate salt, 8.4 mg of fluticasone propionate and 12 g of HFA 134a.

3. Sample Storage Conditions

Each device was stored at 40° C. and 75% relative humidity unless otherwise stated. FPM was determined shortly after preparation ("initial") and after the passage of the indicated time period.

4. Method for Determining FPM

Each MDI canister tested was put into a clean actuator and primed by firing 4 shots. Then 10 shots were fired into an Andersen Cascade Impactor which was quantitatively washed and the amount of drug deposited thereon was quantified by HPLC analysis of the washings. From this the dose delivered (the sum of the amount of drug deposited on the cascade impactor) and the FPM (the sum of drug deposited on stages 3, 4 and 5) data were calculated.

5. Results of FPM Studies with Gaskets from Section 1 Above

TABLE 1

(FPM denotes FP on stages 3, 4, 5, in micrograms)

| Sample | FPM initial (μg) | FPM 2 weeks (μg) | FPM 4 weeks (μg) | FPM 13 weeks (μg) |
|---|---|---|---|---|
| A | 14.0 | 14.4 | 14.0 | 15.0 |
| B | 13.8 | 13.8 | 14.4 | |
| C | 14.3 | 13.0 | 11.8 | |
| D | 13.7 | 13.7 | 14.8 | 14.1 |
| E | 13.4 | 12.8 | 12.5 | |
| G (control) | 12.4 | 10.6 | 9.7 | |

The data in Table 1 show that the initial FPM and the FPM after storage are both higher in an MDI with a gasket treated in accordance with the invention than in the control MDI, which utilized untreated gaskets. The data also show that FPM is more stable in an MDI with that includes a gasket treated in accordance with the invention that in the control MDI.

TABLE 2

(FPM denotes FP on stages 3, 4, 5, in micrograms)

| Sample | FPM initial (µg) | FPM 4 weeks (µg) |
|---|---|---|
| F | 12.5 | 9.7 |
| G (control) | 13.9 | 7.4 |

The data in Table 2 show that the FPM is more stable in an MDI with a gasket treated in accordance with the invention than in the control MDI.

Example 2

1. Treatment of Valve Gaskets

The valves used in the following experiments were DF60 valves from Valois (France). The cap sealing gasket (acrylonitrile butadiene polymer) was removed from the valve for treatment.
Treated Valves The gaskets were extracted at 60° C. with ethanol in a flow-through column. The ethanol was distilled during the process to remove extractable materials, then recycled. Neck gaskets were extracted for 15-24 hours and the stem gaskets were extracted for 4-8 hours. All data are combined in the results.

The gaskets were then re-attached to the valve.
Control

The valve was left untreated.

2. Sample Preparation

The MDIs for which data are presented in FIG. 1 were prepared in aluminium canisters coated with a PTFE/PES polymer blend as described in WO96/32150 and sealed with a valve prepared as described in 1 above. The aluminium canisters contained a pharmaceutical aerosol formulation comprising 4.2 mg of salmeterol in the form of its xinafoate salt, 8.4 mg of fluticasone propionate and 12 g of HFA 134a.

3. Sample Storage Conditions

Each device was stored at 40° C. and 75% relative humidity unless otherwise stated. FPM was determined shortly after preparation ("initial") and after the passage of the indicated time period.

4. Method for Determining FPM

Each MDI canister tested was put into a clean actuator and primed by firing 4 shots. Then 10 shots were fired into an Andersen Cascade Impactor which was quantitatively washed and the amount of drug deposited thereon was quantified by HPLC analysis of the washings. From this the dose delivered (the sum of the amount of drug deposited on the cascade impactor) and the FPM (the sum of drug deposited on stages 3, 4 and 5) data were calculated.

5. Results of FPM Studies (FPM Shown for Fluticasone Propionate (FP))

Figure 3:
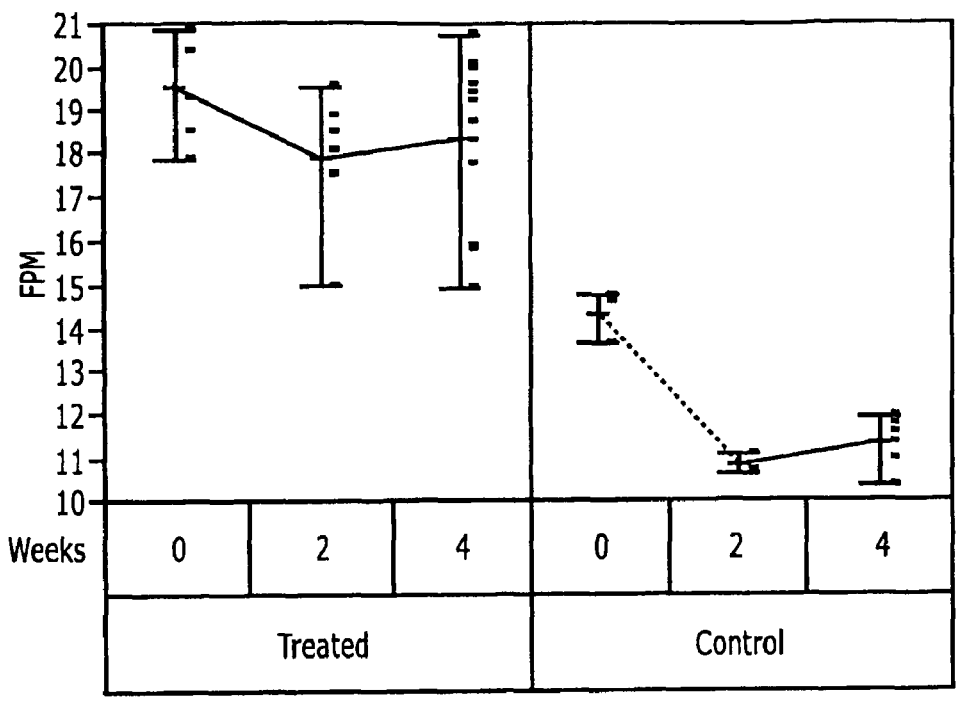

The data in FIG. 3 show that FPM is more stable in an MDI that includes a gasket treated in accordance with the invention than in the control MDI.

Example 3

1. Treatment of Valve Gaskets

The valves used in the following experiments were DF60 valves from Valois (France). The cap sealing gasket (acrylonitrile butadiene polymer) was removed from the valve for treatment.
Treated Valves The cap sealing gaskets were extracted by flowing ethanol (60-80° C.) in a glass column over the gaskets for 24 hours, then dried in a commercial dryer under partial vacuum. The stem gaskets were extracted for 8 hours at 60° C. by the method described in Example 1.

The gasket was then re-attached to the valve.
Control

The valve was left untreated.

2. Sample Preparation

The MDIs for which data are presented in FIG. 3 were prepared in aluminium canisters coated with a PTFE/PES polymer blend as described in WO96/32150 and sealed with a valve prepared as described in 1 above The aluminium canisters contained a pharmaceutical aerosol formulation comprising 4.2 mg of salmeterol in the form of its xinafoate salt, 8.4 mg of fluticasone propionate and 12 g of HFA 134a.

3. Sample Storage Conditions

Each device was stored at room temperature and <30% relative humidity in an inverted orientation (valve down). FPM was determined shortly after preparation ("initial") and after the passage of the indicated time period.

4. Method for Determining FPM

Each MDI canister tested was put into a clean actuator and primed by firing 4 shots. Then 10 shots were fired into an Andersen Cascade Impactor which was quantitatively washed and the amount of drug deposited thereon was quantified by HPLC analysis of the washings. From this the dose delivered (the sum of the amount of drug deposited on the cascade impactor) and the FPM (the sum of drug deposited on stages 3, 4 and 5) data were calculated.

5. Results of FPM Studies (FPM Shown for Fluticasone Propionate (FP))

Figure 4:
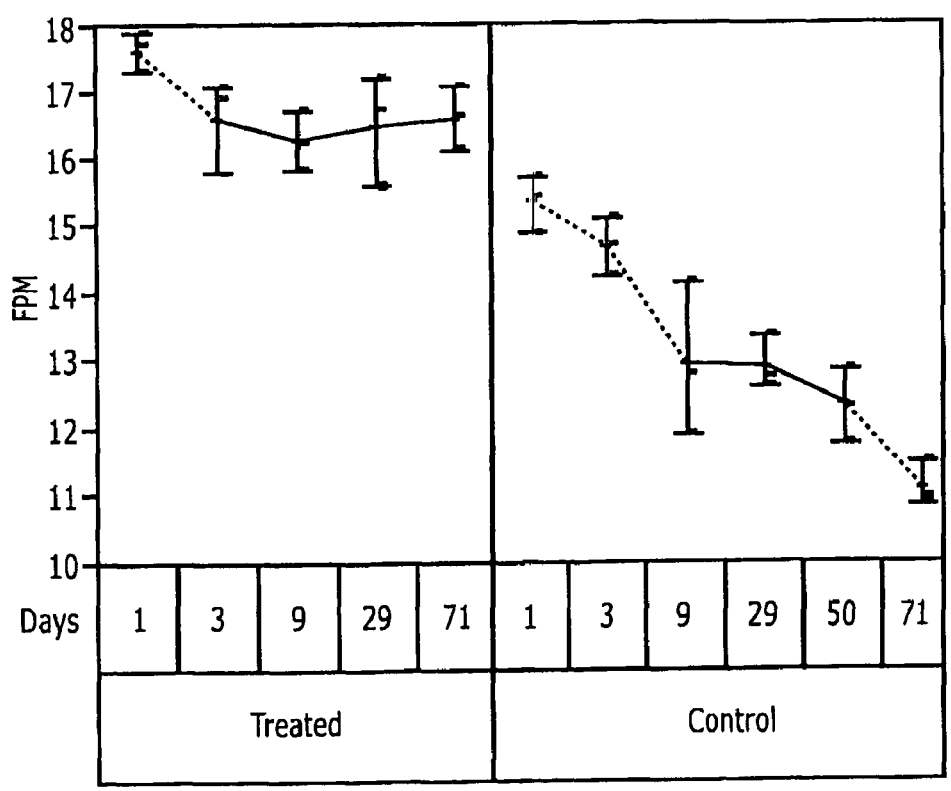

The data in FIG. 4 show that FPM is more stable in an MDI that includes a gasket treated in accordance with the invention than in the control MDI.

Example 4

1. Treatment of Valve Gaskets

The valves used in the following experiments were DF60 valves from Valois (France). The cap sealing gasket and stem sealing gaskets (all acrylonitrile butadiene polymer) were removed from the valve for treatment.

Experiment H

Approximately 10 kg of neck gaskets in a mesh bag were placed into a column. Ethanol at 60° C. was flowed through the column for 4 hours, with the ethanol exiting the column being distilled prior to flowing back into the column. The mesh bag containing the gaskets was removed from the column and placed into an explosion proof dryer, where the gaskets were agitated for 5 minutes at 20° C. The gaskets were then placed back into the column and the processes of ethanol extraction and agitation were repeated four times. The gaskets were then placed back into the column for a final repeat of the extraction process. The gaskets were then removed from the column, rinsed twice with ethanol, and dried in vacuum. Stem gaskets were prepared in a similar manner with total extraction time of 8 hours.

The gasket was then re-attached to the valve.

Experiment I

A 250 ml round bottomed flask was charged with 120 ml ethanol (anhydrous USP grade). 40 neck gaskets were placed in the solution and a condenser was attached to the flask. The solution was then heated under reflux for 1.5 hours with the exclusion of air. The hot ethanol was decanted and the gaskets were re-extracted using the same procedure. The gasket was then washed one time with 50 ml ethanol (anhydrous USP grade), removed from the round bottomed flask and dried in a vacuo over $CaSO_4$. Stem gaskets were extracted in the same manner but for 8 hours.

The gasket was then re-attached to the valve.

Experiment J

Approximately 140,000 neck gaskets were placed in a column. Ethanol at 60° C. was flowed through the column for 24 hours, with the ethanol exiting the column being distilled prior to flowing back into the column. Stem gaskets were extracted in the same manner but for 8 hours.

The gasket was then re-attached to the valve.
Control

The valve was left untreated.

2. Sample Preparation

The MDIs for which data are presented in FIGS. 5-8 were prepared in aluminium canisters coated with a PTFE/PES polymer blend as described in WO96/32150 and sealed with a valve prepared as described in 1 above. The aluminium canisters contained a pharmaceutical aerosol formulation comprising 4.2 mg of salmeterol in the form of its xinafoate salt, 8.4 mg of fluticasone propionate and 12 g of HFA 134a.

3. Sample Storage Conditions

Each device was stored at 40° C. and 75% relative humidity in an inverted orientation (valve down). FPM was determined shortly after preparation ("initial") and after the passage of the indicated time period.

4. Method for Determining FPM

Each MDI canister tested was put into a clean actuator and primed by firing 4 shots. Then 10 shots were fired into an Andersen Cascade Impactor which was quantitatively washed and the amount of drug deposited thereon was quantified by HPLC analysis of the washings. From this the dose delivered (the sum of the amount of drug deposited on the cascade impactor) and the FPM (the sum of drug deposited on stages 3, 4 and 5) data were calculated.

5. Method for Determining Total Fatty Acids (FA)

Fatty acids were determined using a precolumn derivitization with 4-bromophenylacetylbromide, and analyzed via HPLC using a C18 column, ACN gradient, and UV detection at 260 nm.

6. Results of FPM Studies

Figure 5:
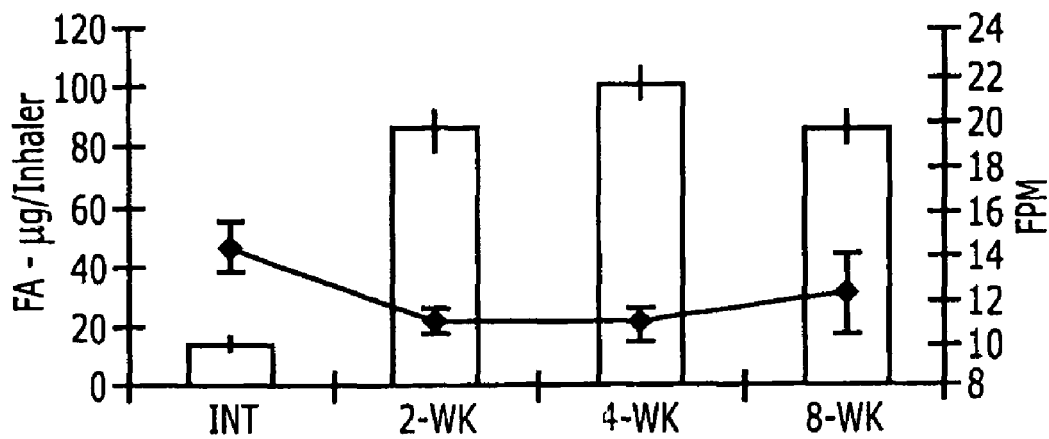
Figure 6:
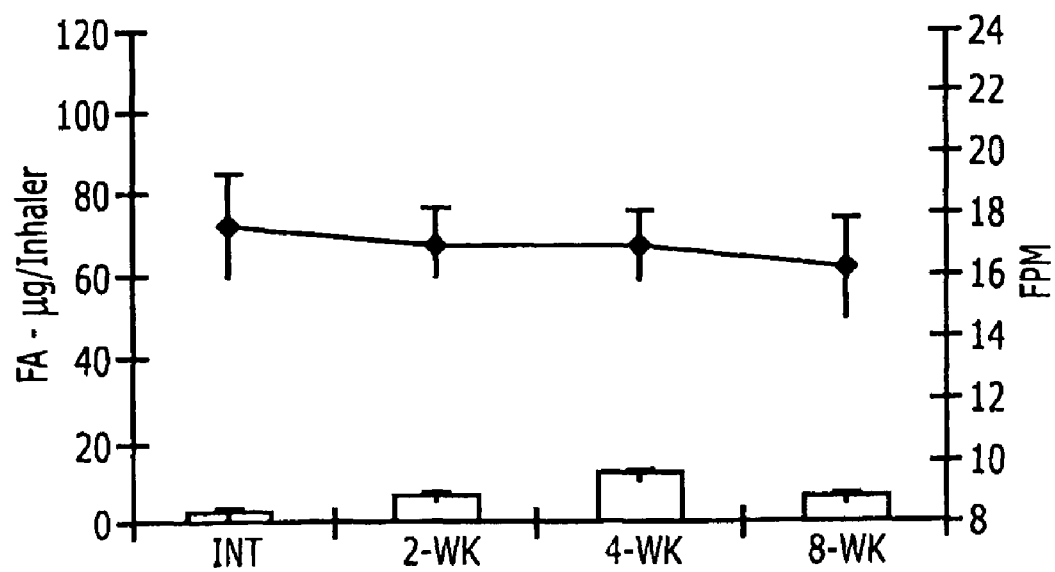
Figure 7:
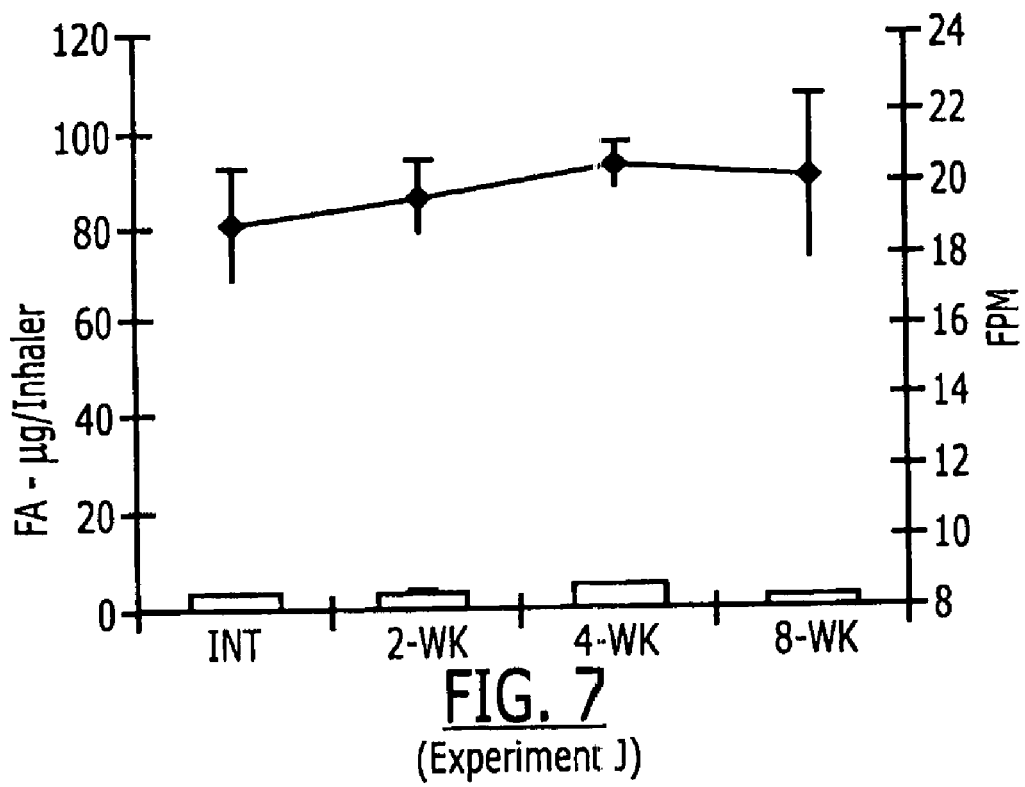
Figure 8:
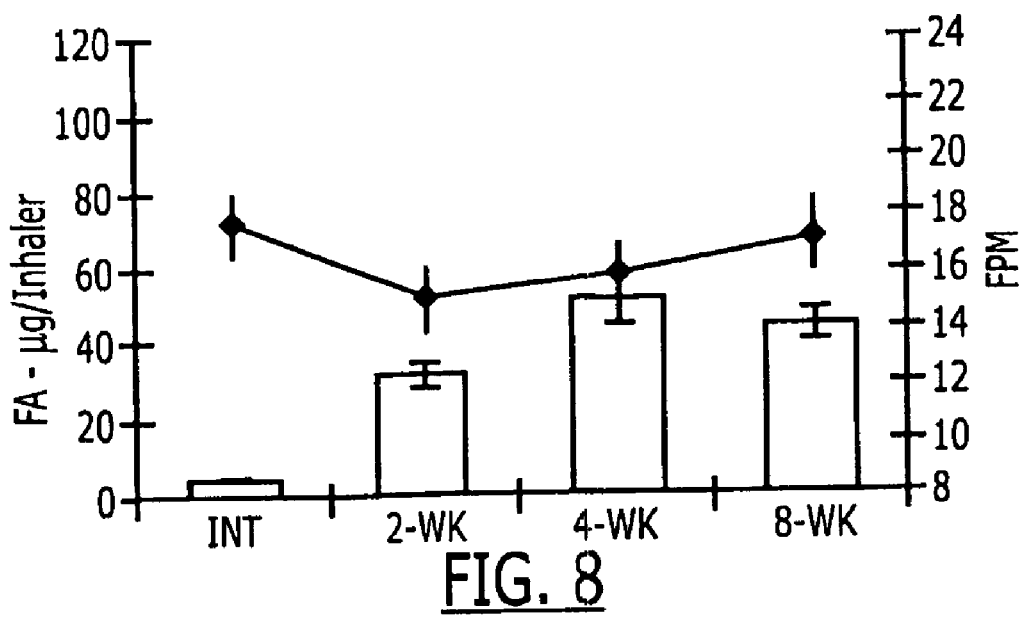

FPM shown for fluticasone propionate (FP)
FA is total fatty acid content in the inhaler
Comparison between the control data in FIG. 5 and the data according to the present invention shown in FIGS. 6-8 illustrate that MDIs that utilize gaskets prepared in accordance with the present invention exhibit more stable FPM than conventional MDIs that utilize untreated gaskets. The data in FIGS. 5-8 also illustrate that there is a correlation between the total fatty acid content in the aerosol pharmaceutical formulation and the resulting FPM of the formulation.

Example 5

1. Treatment of Valve Gaskets

The valves used in the following experiments were MK96 valves from Valois (France). The cap sealing gasket (EPDM) was removed from the valve for treatment.

Experiment K

Approximately 140,000 neck gaskets were placed in a column. Ethanol at 60° C. was flowed through the column for 24 hours, with the ethanol exiting the column being distilled prior to flowing back into the column.

The gasket was then re-attached to the valve.
Control

The valve was left untreated. Control is provided for comparison purposes and is not part of the present invention.

2. Sample Preparation

The MDIs for which data are presented in Tables 3 and 4 were prepared in aluminium canisters coated with a PTFE/PES polymer blend as described in WO96/32150 and sealed with a valve prepared as described in 1 above. The aluminium canisters contained a pharmaceutical aerosol formulation comprising 4.2 mg of salmeterol in the form of its xinafoate salt, 8.4 mg of fluticasone propionate and 12 g of HFA 134a. For each storage condition, the control and Experiment K, canisters were filled from the same suspension.

3. Sample Storage Conditions

Each device was stored at the indicated conditions. Permeability and leak rate were determined at initial time point from weight change over 7 days at ambient storage and determined by weight change during storage at all other timepoints.

4. Method for Permeability

Samples are stored at controlled temperature and relative humidity conditions (as specified in the tables) for the indicated period of time then assay for moisture using a modified Karl Fischer titration.

5. Method for Determining Leak Rate

Samples are weighed and stored at the indicated conditions. At the end of the test period, the samples are reweighed and a leak rate is calculated from the difference in initial weight and the weight at the test date, divided by time, and normalized to mg of propellant leaked/year of storage.

6. Results

TABLE 3

Comparative permeability data for salmeterol/fluticasone propionate MDI, water content (ppm)

| Time (months) | Product strength | Control | Experiment K |
|---|---|---|---|
| | | Storage conditions 25° C. ± 2° C./ 60% ± 5% RH | |
| Initial | 25/50 μg | 90 | 90 |
| | 25/125 μg | 101 | 80 |
| | 25/250 μg | 85 | 96 |
| 3 | 25/50 μg | 187 | 158 |
| | 25/125 μg | 161 | 146 |
| | 25/250 μg | 158 | 157 |
| | | Storage conditions 40° C. ± 2° C./ 75% ± 5% RH | |
| 1 | 25/50 μg | 211 | 205 |
| | 25/125 μg | 212 | 205 |
| | 25/250 μg | 212 | 208 |
| 3 | 25/50 μg | 296 | 293 |
| | 25/125 μg | 310 | 296 |
| | 25/250 μg | 289 | 301 |

TABLE 4

Comparative permeability data for salmeterol/fluticasone propionate MDI, leak rate (mg/year)

| Time (months) | Product strength | Control | Experiment K |
|---|---|---|---|
| | | Storage conditions 30° C. ± 2° C./ 65% ± 5% RH | |
| Initial | 25/50 μg | 82 | 108 |
| | 25/125 μg | 110 | 120 |
| | 25/250 μg | 107 | 112 |
| 4 | 25/50 μg | 208 | 204 |
| | 25/125 μg | 196 | 199 |
| | 25/250 μg | 191 | 194 |
| | | Storage conditions 40° C. ± 2° C./ 75% ± 5% RH | |
| 1 | 25/50 μg | 295 | 305 |
| | 25/125 μg | 295 | 309 |
| | 25/250 μg | 301 | 307 |
| 4 | 25/50 μg | 407 | 435 |
| | 25/125 μg | 407 | 412 |
| | 25/250 μg | 411 | 423 |

These data show that the physical properties of the gasket, which allow the gasket to act as a sealing gasket in an MDI, are not adversely effected by ethanol extraction of the neck gasket.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims.

What is claimed is:

1. A method of manufacturing a metered dose inhaler (MDI), said method comprising:
    contacting an elastomeric gasket material comprising acrylonitrile butadiene rubber and one or more extractable compounds including oleic acid, with a solution comprising a lower alcohol, wherein the solution is at a temperature of at least 40° C. to extract oleic acid from the elastomeric gasket material such that the gasket material comprises between about 0.04 and 0.17% oleic acid to form a MDI sealing gasket;
    agitating the elastomeric gasket material and the solution, wherein the agitating of the elastomeric gasket material is performed subsequent to the contacting of the elastomeric gasket material with the solution;
    providing other MDI components and a pharmaceutical aerosol formulation comprising salmeterol xianfoate and fluticasone propionate; and
    assembling the MDI.

2. The method of claim 1, wherein at least one of the one or more extractable compounds comprises at least one additional compound selected from the group consisting of nonylphenol isomers, 2,2'-methylenebis(6-tertbutyl-4-methylphenol), 2,2,4,6,6-pentamethylhept-3-ene, 3'-oxybispropanitrile, palmitic acid, and stearic acid.

3. The method of claim 1, wherein the lower alcohol is ethanol or isopropanol.

4. The method of claim 1, wherein the solution consists essentially of ethanol.

5. The method of claim 1, wherein the elastomeric gasket material is contacted with the solution for 15 minutes or greater.

6. The method of claim 1, wherein the elastomeric gasket material is contacted with the solution at a temperature of at least 60° C.

7. The method of claim 1, wherein the elastomeric gasket material is contacted with the solution under reflux conditions for the solution.

8. The method of claim 1, wherein the elastomeric gasket material is contacted with the solution under conditions sufficient to extract at least 20 percent of at least one of the one or more extractable compounds.

9. The method of claim 1, wherein the elastomeric gasket material is contacted with the solution under conditions sufficient to extract at least 40 percent of at least one of the one or more extractable compounds.

10. A method of manufacturing a metered dose inhaler (MDI), said method comprising:
    contacting an elastomeric gasket material comprising acrylonitrile butadiene rubber and one or more extractable compounds including oleic acid, with a solution comprising a lower alcohol, wherein the solution is at a temperature of at least 40° C. to extract oleic acid from the elastomeric gasket material such that the gasket material comprises between about 0.04 and 0.17% oleic acid to form a MDI sealing gasket;
    agitating the elastomeric gasket material and the solution;
    providing other MDI components and a pharmaceutical aerosol formulation comprising salmeterol xianfoate and fluticasone propionate; and
    assembling the MDI;
    wherein the contacting of the elastomeric gasket material with the solution occurs subsequent to the agitating of the elastomeric gasket material.

11. The method of claim 10, wherein at least one of the one or more extractable compounds comprises at least one additional compound selected from the group consisting of nonylphenol isomers, 2,2'-methylenebis(6-tertbutyl-4-methylphenol), 2,2,4,6,6-pentamethylhept-3-ene, 3'-oxybispropanitrile, palmitic acid, and stearic acid.

12. The method of claim 10, wherein the lower alcohol is ethanol or isopropanol.

13. The method of claim 10, wherein the solution consists essentially of ethanol.

14. The method of claim 10, wherein the elastomeric gasket material is contacted with the solution for 15 minutes or greater.

15. The method of claim 10, wherein the elastomeric gasket material is contacted with the solution at a temperature of at least 60° C.

16. The method of claim 10, wherein the elastomeric gasket material is contacted with the solution under reflux conditions for the solution.

17. The method of claim 10, wherein the elastomeric gasket material is contacted with the solution under conditions sufficient to extract at least 20 percent of at least one of the one or more extractable compounds.

18. The method of claim 10, wherein the elastomeric gasket material is contacted with the solution under conditions sufficient to extract at least 40 percent of at least one of the one or more extractable compounds.

19. A method of manufacturing a metered dose inhaler (MDI), said method comprising:
   contacting an elastomeric gasket material comprising acrylonitrile butadiene rubber and one or more extractable compounds including oleic acid, with a solution comprising a lower alcohol, wherein the solution is at a temperature of at least 40° C. to extract oleic acid from the elastomeric gasket material such that the gasket material comprises between about 0.04 and 0.17% oleic acid to form a MDI sealing gasket;
   agitating the elastomeric gasket material and the solution;
   drying the elastomeric gasket material, wherein said drying step comprises exposing the elastomeric gasket material to a vacuum, providing other MDI components and a pharmaceutical aerosol formulation comprising salmeterol xianfoate and fluticasone propionate; and
   assembling the MDI.

20. The method of claim 19, wherein at least one of the one or more extractable compounds comprises at least one additional compound selected from the group consisting of nonylphenol isomers, 2,2'-methylenebis(6-tertbutyl-4-methylphenol), 2,2,4,6,6-pentamethylhept-3-ene, 3'-oxybispropanitrile, palmitic acid, and stearic acid.

21. The method of claim 19, wherein the lower alcohol is ethanol or isopropanol.

22. The method of claim 19, wherein the solution consists essentially of ethanol.

23. The method of claim 19, wherein the elastomeric gasket material is contacted with the solution for 15 minutes or greater.

24. The method of claim 19, wherein the elastomeric gasket material is contacted with the solution at a temperature of at least 60° C.

25. The method of claim 19, wherein the elastomeric gasket material is contacted with the solution under reflux conditions for the solution.

26. The method of claim 19, wherein the elastomeric gasket material is contacted with the solution under conditions sufficient to extract at least 20 percent of at least one of the one or more extractable compounds.

27. The method of claim 19, wherein the elastomeric gasket material is contacted with the solution under conditions sufficient to extract at least 40 percent of at least one of the one or more extractable compounds.

28. A method of manufacturing a metered dose inhaler (MDI), said method comprising:
   contacting an elastomeric gasket material comprising acrylonitrile butadiene rubber and one or more extractable compounds including oleic acid, with a solution consists of a lower alcohol, wherein the solution is at a temperature of at least 40° C. to extract oleic acid from the elastomeric gasket material such that the gasket material comprises between about 0.04 and 0.17% oleic acid to form a MDI sealing gasket;
   agitating the elastomeric gasket material and the solution;
   drying the elastomeric gasket material, wherein said drying step comprises exposing the elastomeric gasket material to a vacuum, providing other MDI components and a pharmaceutical aerosol formulation comprising salmeterol xianfoate and fluticasone propionate; and
   assembling the MDI.

* * * * *